Figure 1:
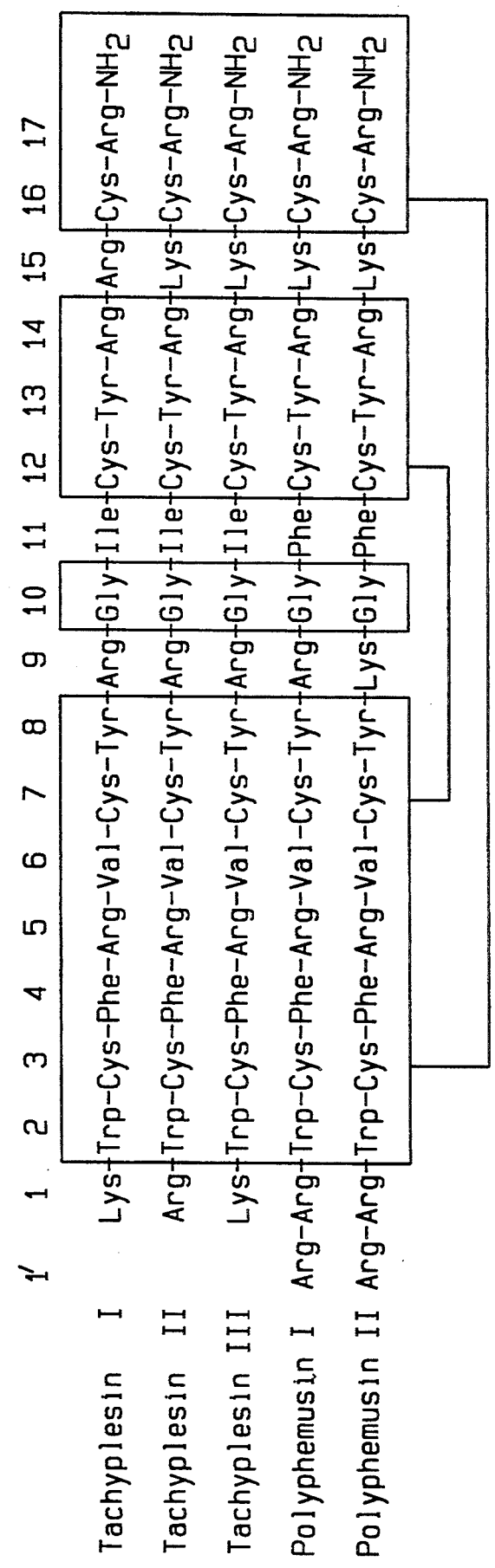

United States Patent [19]

Fujii et al.

[11] Patent Number: 5,449,752

[45] Date of Patent: Sep. 12, 1995

[54] POLYPEPTIDES WITH AFFINITY TO LIPOPOLYSACCHARIDES AND THEIR USES

[75] Inventors: Nobutaka Fujii, Osaka; Naoki Yamamoto, Tokyo; Akiyoshi Matsumoto, Tokyo; Michinori Waki, Tokyo, all of Japan

[73] Assignee: Seikagaku Kogyo K.K., Tokyo, Japan

[21] Appl. No.: 876,883

[22] Filed: Apr. 29, 1992

[30] Foreign Application Priority Data

May 2, 1991 [JP] Japan ................... 3-130410
Apr. 28, 1992 [JP] Japan ................... 4-134374

[51] Int. Cl.$^6$ ............... A61K 38/00; C07K 5/00; C07K 7/00; C07K 15/00
[52] U.S. Cl. .................................................. 530/326
[58] Field of Search ................. 530/326; 514/13, 14

[56] References Cited

FOREIGN PATENT DOCUMENTS

9204374 3/1992 WIPO ..................... C07K 4/08

OTHER PUBLICATIONS

Mitsuya et al., Proc. Natl. Acad. Sci., vol. 82, Oct. 1985, pp. 7096–7100.

Shigenaga et al., 1990, Antimicrobial tachyplesin peptide precursor, J. Biol. Chem. 265:21350–21354.

Kawano et al., 1990, Antimicrobial peptide, tachplesin I, isolated from hemocytes of the horseshoe crab (*tachypleus tridentatus*), J. Biol. Chem. 265:15365–15367.

Muta et al., 1990, Tachyplesins isolated from hemocytes of Southeast Asian horseshoe crabs (*carcinoscorpius rotundicauda* and *tachypleus gigas*): identification of a new tachyplesin, tachyplesin III, and a processing intermediate of its precursor, J. Biochem. 108:261–266.

Japanese Laid-Open Patent Publication No. 167230/1990 and its English abstract.

Japanese Laid-Open Patent Publication No. 152987/1990 and its English abstract.

Japanese Laid-Open Patent Publication No. 53799/1990 and its English abstract.

Published Searched Application No. 500194/1990 and its English abstract.

Miyata et al., 1989, Antimicrobial peptides, isolated from horseshoe crab hemocytes, tachyplesin II, and polyphemusins I and II: chemical structures and biological activity, J. Biochem. 106:663–668.

Akaji et al., 1989, Studies on peptides. CLXVIII. Syntheses of three peptides isolated from horseshoe crab hemocytes, tachyplesin I, tachyplesin II, and polyphemusin I, Chem. Pharm. Bull. 37:2661–2664.

Taisha, 1989, Metabolism 26:429–439 and its English abstract.

(List continued on next page.)

*Primary Examiner*—Jill Warden
*Assistant Examiner*—A. M. Davenport
*Attorney, Agent, or Firm*—Pennie & Edmonds

[57] ABSTRACT

A novel polypeptide sequence having the formula $$\begin{array}{cccccccccccc} 1 & 2 & 3 & 4 & 5 & 6 & 7 & 8 & 9 & 10 & 11 \\ A_1 - & A_2 - & Cys - & A_2 - & A_3 - & A_3 - & Cys - & A_2 - & A_3 - & Gly - & A_2 - \end{array}$$

$$\begin{array}{cccccc} 12 & 13 & 14 & 15 & 16 & 17 & 18 \\ Cys - & A_2 - & A_3 - & A_3 - & Cys - & A_4 - & A_5 \end{array}$$

in which $A_1$ is a hydrogen or at least one and no more than two amino acids selected from the group consisting of lysine and arginine, $A_2$ is a tyrosine, phenylalanine or tryptophan residue, $A_3$ is an arginine or lysine residue, $A_4$ is at least one and no more than two amino acids selected from the group consisting of lysine and arginine, and $A_5$ is an —OH or an $NH_2$, is described.

The polypeptide may be used in a pharmaceutical composition as an antimicrobial or antiviral agent, specifically as an anti-HIV agent.

9 Claims, 2 Drawing Sheets

OTHER PUBLICATIONS

Shieh et al., 1989, Synthesis and properties of tachyplesin I, a lipopolysaccharide-binding peptide, from *tachypleus tridentatus*, FEBS Lett. 252:121–124.

Nakamura et al., 1988, Tachyplesin, a class of antimicrobial peptide from the hemocytes of the horseshoe crab (*tachypleus tridentatus*), J. Biol. Chem. 263:16709–16713.

Murakami et al., 1991, Direct virus inactivation of tachyplesin I and its isopeptides from horseshoe crab hemocytes, Chemotherapy 37:327–334.

Morimoto et al., 1991, Inhibitory effect of tachyplesin I on the proliferation of human immunodeficiency virus *in vitro*, Chemotherapy 37:206–211.

Nakashima et al., Mar. 1992, Anti-Human Immunodeficiency Virus Activity of a Novel Synthetic Polypeptide, T22 ([Tyr$^{5,12}$, Lys$^7$]polyphemusin II)–A Possible Inhibitor for Virus-Cell Fusion, *Antiviral Research*, 17 (Sup. 1):71.

European Search Report for EP Appln. No. 92107509, dated 5 Aug. 1992.

SEQUENCE LISTING ( 1 ) GENERAL INFORMATION:

( i i i ) NUMBER OF SEQUENCES: 39

( 2 ) INFORMATION FOR SEQ ID NO:1:

( i ) SEQUENCE CHARACTERISTICS:
( A ) LENGTH: 17 amino acids
( B ) TYPE: amino acid
( C ) STRANDEDNESS: single
( D ) TOPOLOGY: unknown ( i i ) MOLECULE TYPE: peptide ( x i ) SEQUENCE DESCRIPTION: SEQ ID NO:1:

Lys Trp Cys Phe Arg Val Cys Tyr Arg Gly Ile Cys Tyr Arg Arg Cys
1               5                   10                  15

Arg ( 2 ) INFORMATION FOR SEQ ID NO:2:

( i ) SEQUENCE CHARACTERISTICS:
( A ) LENGTH: 17 amino acids
( B ) TYPE: amino acid
( C ) STRANDEDNESS: single
( D ) TOPOLOGY: unknown ( i i ) MOLECULE TYPE: peptide ( x i ) SEQUENCE DESCRIPTION: SEQ ID NO:2:

Arg Trp Cys Phe Arg Val Cys Tyr Arg Gly Ile Cys Tyr Arg Lys Cys
1               5                   10                  15

Arg ( 2 ) INFORMATION FOR SEQ ID NO:3:

( i ) SEQUENCE CHARACTERISTICS:
( A ) LENGTH: 17 amino acids
( B ) TYPE: amino acid (C) STRANDEDNESS: single
(D) TOPOLOGY: unknown (ii) MOLECULE TYPE: peptide (xi) SEQUENCE DESCRIPTION: SEQ ID NO:3:

Lys Trp Cys Phe Arg Val Cys Tyr Arg Gly Ile Cys Tyr Arg Lys Cys
1               5                   10                  15

Arg (2) INFORMATION FOR SEQ ID NO:4:

(i) SEQUENCE CHARACTERISTICS:
        (A) LENGTH: 18 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:4:

Arg Arg Trp Cys Phe Arg Val Cys Tyr Arg Gly Phe Cys Tyr Arg Lys
1               5                   10                  15

Cys Arg (2) INFORMATION FOR SEQ ID NO:5:

(i) SEQUENCE CHARACTERISTICS:
        (A) LENGTH: 18 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:5:

Arg Arg Trp Cys Phe Arg Val Cys Tyr Lys Gly Phe Cys Tyr Arg Lys
1               5                   10                  15

Cys Arg (2) INFORMATION FOR SEQ ID NO:6:

(i) SEQUENCE CHARACTERISTICS:
        (A) LENGTH: 18 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other or amino acid
        (B) LOCATION: 1
        (D) OTHER INFORMATION: /label=X
            / note="X =hydrogen or lys and/or arg"

(ix) FEATURE:
        (A) NAME/KEY: Amino acid
        (B) LOCATION: 2
        (D) OTHER INFORMATION: /label=X
            / note="X =tyr, phe or trp"

(ix) FEATURE:
        (A) NAME/KEY: Amino acid
        (B) LOCATION: 4
        (D) OTHER INFORMATION: /label=X
            / note="X =tyr, phe or trp"

(ix) FEATURE:
        (A) NAME/KEY: Amino acid
        (B) LOCATION: 5
        (D) OTHER INFORMATION: /label=X
            / note="X =arg or lys"

( i x ) FEATURE:
    ( A ) NAME/KEY: Amino acid
    ( B ) LOCATION: 6
    ( D ) OTHER INFORMATION: /label=X
        / note="X =arg or lys"

( i x ) FEATURE:
    ( A ) NAME/KEY: Amino acid
    ( B ) LOCATION: 8
    ( D ) OTHER INFORMATION: /label=X
        / note="X =tyr, phe or trp"

( i x ) FEATURE:
    ( A ) NAME/KEY: Amino acid
    ( B ) LOCATION: 9
    ( D ) OTHER INFORMATION: /label=X
        / note="X =arg or lys"

( i x ) FEATURE:
    ( A ) NAME/KEY: Amino acid
    ( B ) LOCATION: 11
    ( D ) OTHER INFORMATION: /label=X
        / note="X =tyr, phe or trp"

( i x ) FEATURE:
    ( A ) NAME/KEY: Amino acid
    ( B ) LOCATION: 13
    ( D ) OTHER INFORMATION: /label=X
        / note="X =tyr, phe or trp"

( i x ) FEATURE:
    ( A ) NAME/KEY: Amino acid
    ( B ) LOCATION: 14
    ( D ) OTHER INFORMATION: /label=X
        / note="X =arg or lys"

( i x ) FEATURE:
    ( A ) NAME/KEY: Amino acid
    ( B ) LOCATION: 15
    ( D ) OTHER INFORMATION: /label=X
        / note="X =arg or lys"

( i x ) FEATURE:
    ( A ) NAME/KEY: Amino acid
    ( B ) LOCATION: 17
    ( D ) OTHER INFORMATION: /label=X
        / note="X =lys and/or arg"

( i x ) FEATURE:
    ( A ) NAME/KEY: Other
    ( B ) LOCATION: 18
    ( D ) OTHER INFORMATION: /label=X
        / note="X =-OH or -NH2"

( x i ) SEQUENCE DESCRIPTION: SEQ ID NO:6:

```
Xaa  Xaa  Cys  Xaa  Xaa  Xaa  Cys  Xaa  Xaa  Gly  Xaa  Cys  Xaa  Xaa  Xaa  Cys
1                  5                        10                       15

Xaa  Xaa
```

( 2 ) INFORMATION FOR SEQ ID NO:7:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:7:

```
Arg  Arg  Trp  Cys  Tyr  Arg  Lys  Cys  Tyr  Lys  Gly  Tyr  Cys  Tyr  Arg  Lys
1                  5                        10                       15

Cys  Arg
```

( 2 ) INFORMATION FOR SEQ ID NO:8:

( i ) SEQUENCE CHARACTERISTICS:
  ( A ) LENGTH: 19 amino acids
  ( B ) TYPE: amino acid
  ( C ) STRANDEDNESS: single
  ( D ) TOPOLOGY: unknown ( i i ) MOLECULE TYPE: peptide ( x i ) SEQUENCE DESCRIPTION: SEQ ID NO:8:

Arg Arg Trp Cys Tyr Arg Lys Cys Tyr Lys Gly Tyr Cys Tyr Arg Lys
1               5                   10                  15

Cys Arg Arg ( 2 ) INFORMATION FOR SEQ ID NO:9:

( i ) SEQUENCE CHARACTERISTICS:
    ( A ) LENGTH: 17 amino acids
    ( B ) TYPE: amino acid
    ( C ) STRANDEDNESS: single
    ( D ) TOPOLOGY: unknown ( i i ) MOLECULE TYPE: peptide ( x i ) SEQUENCE DESCRIPTION: SEQ ID NO:9:

Arg Trp Cys Tyr Arg Lys Cys Tyr Lys Gly Phe Cys Tyr Arg Lys Cys
1               5                   10                  15

Arg ( 2 ) INFORMATION FOR SEQ ID NO:10:

( i ) SEQUENCE CHARACTERISTICS:
    ( A ) LENGTH: 18 amino acids
    ( B ) TYPE: amino acid
    ( C ) STRANDEDNESS: single
    ( D ) TOPOLOGY: unknown ( i i ) MOLECULE TYPE: peptide ( x i ) SEQUENCE DESCRIPTION: SEQ ID NO:10:

Arg Trp Cys Tyr Arg Lys Cys Tyr Lys Gly Phe Cys Tyr Arg Lys Cys
1               5                   10                  15

Arg Arg ( 2 ) INFORMATION FOR SEQ ID NO:11:

( i ) SEQUENCE CHARACTERISTICS:
    ( A ) LENGTH: 18 amino acids
    ( B ) TYPE: amino acid
    ( C ) STRANDEDNESS: single
    ( D ) TOPOLOGY: unknown ( i i ) MOLECULE TYPE: peptide ( x i ) SEQUENCE DESCRIPTION: SEQ ID NO:11:

Arg Arg Trp Cys Trp Arg Lys Cys Tyr Lys Gly Tyr Cys Trp Arg Lys
1               5                   10                  15

Cys Arg ( 2 ) INFORMATION FOR SEQ ID NO:12:

( i ) SEQUENCE CHARACTERISTICS:
    ( A ) LENGTH: 18 amino acids
    ( B ) TYPE: amino acid
    ( C ) STRANDEDNESS: single
    ( D ) TOPOLOGY: unknown ( i i ) MOLECULE TYPE: peptide ( x i ) SEQUENCE DESCRIPTION: SEQ ID NO:12:

Arg Arg Trp Cys Trp Arg Lys Cys Trp Lys Gly Trp Cys Trp Arg Lys
1               5                   10                  15

Cys Arg ( 2 ) INFORMATION FOR SEQ ID NO:13:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:13:

Arg Arg Tyr Cys Tyr Arg Lys Cys Tyr Lys Gly Tyr Cys Trp Arg Lys
1               5                   10                  15

Cys Arg ( 2 ) INFORMATION FOR SEQ ID NO:14:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:14:

Arg Arg Tyr Cys Tyr Arg Lys Cys Tyr Lys Gly Tyr Cys Tyr Arg Lys
1               5                   10                  15

Cys Arg Arg ( 2 ) INFORMATION FOR SEQ ID NO:15:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:15:

Arg Arg Trp Cys Tyr Lys Lys Cys Tyr Lys Gly Tyr Cys Tyr Lys Lys
1               5                   10                  15

Cys Arg ( 2 ) INFORMATION FOR SEQ ID NO:16:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:16:

Lys Lys Trp Cys Tyr Lys Lys Cys Tyr Lys Gly Tyr Cys Tyr Lys Lys
1               5                   10                  15

Cys Lys ( 2 ) INFORMATION FOR SEQ ID NO:17:

( i ) SEQUENCE CHARACTERISTICS:

(A) LENGTH: 19 amino acids
(B) TYPE: amino acid
(C) STRANDEDNESS: single
(D) TOPOLOGY: unknown (ii) MOLECULE TYPE: peptide (xi) SEQUENCE DESCRIPTION: SEQ ID NO:17:

Lys Lys Trp Cys Tyr Lys Lys Cys Tyr Lys Gly Tyr Cys Tyr Lys Lys
1               5                   10                  15
Cys Lys Lys (2) INFORMATION FOR SEQ ID NO:18:

(i) SEQUENCE CHARACTERISTICS:
    (A) LENGTH: 18 amino acids
    (B) TYPE: amino acid
    (C) STRANDEDNESS: single
    (D) TOPOLOGY: unknown (ii) MOLECULE TYPE: peptide (xi) SEQUENCE DESCRIPTION: SEQ ID NO:18:

Arg Arg Trp Cys Tyr Lys Arg Cys Tyr Lys Gly Tyr Cys Tyr Lys Arg
1               5                   10                  15
Cys Arg (2) INFORMATION FOR SEQ ID NO:19:

(i) SEQUENCE CHARACTERISTICS:
    (A) LENGTH: 18 amino acids
    (B) TYPE: amino acid
    (C) STRANDEDNESS: single
    (D) TOPOLOGY: unknown (ii) MOLECULE TYPE: peptide (xi) SEQUENCE DESCRIPTION: SEQ ID NO:19:

Arg Arg Trp Cys Tyr Arg Lys Cys Tyr Lys Gly Phe Cys Tyr Arg Lys
1               5                   10                  15
Cys Arg (2) INFORMATION FOR SEQ ID NO:20:

(i) SEQUENCE CHARACTERISTICS:
    (A) LENGTH: 18 amino acids
    (B) TYPE: amino acid
    (C) STRANDEDNESS: single
    (D) TOPOLOGY: unknown (ii) MOLECULE TYPE: peptide (xi) SEQUENCE DESCRIPTION: SEQ ID NO:20:

Arg Arg Trp Cys Tyr Arg Lys Cys Tyr Arg Gly Tyr Cys Tyr Arg Lys
1               5                   10                  15
Cys Arg (2) INFORMATION FOR SEQ ID NO:21:

(i) SEQUENCE CHARACTERISTICS:
    (A) LENGTH: 17 amino acids
    (B) TYPE: amino acid
    (C) STRANDEDNESS: single
    (D) TOPOLOGY: unknown (ii) MOLECULE TYPE: peptide (xi) SEQUENCE DESCRIPTION: SEQ ID NO:21:

Arg Trp Cys Tyr Arg Lys Cys Tyr Arg Gly Tyr Cys Tyr Arg Lys Cys

```
     1               5                    1 0                     1 5
```

Arg ( 2 ) INFORMATION FOR SEQ ID NO:22:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:22:

```
Arg Arg Trp Cys Tyr Arg Lys Cys Phe Arg Gly Phe Cys Tyr Arg Lys
 1               5                    1 0                     1 5

Cys Arg
```

( 2 ) INFORMATION FOR SEQ ID NO:23:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:23:

```
Arg Trp Cys Tyr Arg Lys Cys Phe Arg Gly Phe Cys Tyr Arg Lys Cys
 1               5                    1 0                     1 5

Arg
```

( 2 ) INFORMATION FOR SEQ ID NO:24:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:24:

```
Arg Arg Trp Cys Tyr Lys Arg Cys Tyr Arg Gly Phe Cys Tyr Lys Arg
 1               5                    1 0                     1 5

Cys Arg
```

( 2 ) INFORMATION FOR SEQ ID NO:25:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:25:

```
Arg Trp Cys Tyr Arg Lys Cys Tyr Arg Gly Phe Cys Tyr Arg Lys Cys
 1               5                    1 0                     1 5

Arg
```

( 2 ) INFORMATION FOR SEQ ID NO:26:

( i ) SEQUENCE CHARACTERISTICS:
        ( A ) LENGTH: 18 amino acids
        ( B ) TYPE: amino acid (C) STRANDEDNESS: single
(D) TOPOLOGY: unknown (ii) MOLECULE TYPE: peptide (xi) SEQUENCE DESCRIPTION: SEQ ID NO:26:

Arg Arg Trp Cys Tyr Arg Lys Cys Phe Lys Gly Phe Cys Tyr Arg Lys
1               5                   10                  15
Cys Arg (2) INFORMATION FOR SEQ ID NO:27:

(i) SEQUENCE CHARACTERISTICS:
      (A) LENGTH: 17 amino acids
      (B) TYPE: amino acid
      (C) STRANDEDNESS: single
      (D) TOPOLOGY: unknown (ii) MOLECULE TYPE: peptide (xi) SEQUENCE DESCRIPTION: SEQ ID NO:27:

Arg Trp Cys Tyr Arg Lys Cys Phe Lys Gly Phe Cys Tyr Arg Lys Cys
1               5                   10                  15
Arg (2) INFORMATION FOR SEQ ID NO:28:

(i) SEQUENCE CHARACTERISTICS:
      (A) LENGTH: 19 amino acids
      (B) TYPE: amino acid
      (C) STRANDEDNESS: single
      (D) TOPOLOGY: unknown (ii) MOLECULE TYPE: peptide (xi) SEQUENCE DESCRIPTION: SEQ ID NO:28:

Arg Arg Trp Cys Tyr Arg Lys Cys Phe Lys Gly Phe Cys Tyr Arg Lys
1               5                   10                  15
Cys Arg Arg (2) INFORMATION FOR SEQ ID NO:29:

(i) SEQUENCE CHARACTERISTICS:
      (A) LENGTH: 18 amino acids
      (B) TYPE: amino acid
      (C) STRANDEDNESS: single
      (D) TOPOLOGY: unknown (ii) MOLECULE TYPE: peptide (xi) SEQUENCE DESCRIPTION: SEQ ID NO:29:

Arg Arg Trp Cys Tyr Lys Arg Cys Phe Lys Gly Phe Cys Tyr Lys Arg
1               5                   10                  15
Cys Arg (2) INFORMATION FOR SEQ ID NO:30:

(i) SEQUENCE CHARACTERISTICS:
      (A) LENGTH: 18 amino acids
      (B) TYPE: amino acid
      (C) STRANDEDNESS: single
      (D) TOPOLOGY: unknown (ii) MOLECULE TYPE: peptide (xi) SEQUENCE DESCRIPTION: SEQ ID NO:30:

Arg Arg Trp Cys Tyr Lys Arg Cys Tyr Arg Gly Tyr Cys Tyr Lys Arg
1               5                   10                  15

Cys Arg ( 2 ) INFORMATION FOR SEQ ID NO:31:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:31:

```
Arg Arg Trp Cys Tyr Arg Arg Cys Tyr Lys Gly Tyr Cys Tyr Arg Arg
1               5                   10                  15
Cys Arg
```

( 2 ) INFORMATION FOR SEQ ID NO:32:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:32:

```
Arg Trp Cys Tyr Arg Lys Cys Tyr Lys Gly Tyr Cys Tyr Arg Lys Cys
1               5                   10                  15
Arg
```

( 2 ) INFORMATION FOR SEQ ID NO:33:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:33:

```
Trp Cys Tyr Arg Lys Cys Tyr Lys Gly Tyr Cys Tyr Arg Lys Cys Arg
1               5                   10                  15
```

( 2 ) INFORMATION FOR SEQ ID NO:34:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:34:

```
Trp Cys Tyr Arg Lys Cys Tyr Lys Gly Phe Cys Tyr Arg Lys Cys Arg
1               5                   10                  15
```

( 2 ) INFORMATION FOR SEQ ID NO:35:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:35:

```
    Trp  Cys  Tyr  Arg  Lys  Cys  Phe  Arg  Gly  Phe  Cys  Tyr  Arg  Lys  Cys  Arg
    1              5                        10                       15
```

(2) INFORMATION FOR SEQ ID NO:36:

(i) SEQUENCE CHARACTERISTICS:
       (A) LENGTH: 16 amino acids
       (B) TYPE: amino acid
       (C) STRANDEDNESS: single
       (D) TOPOLOGY: unknown (ii) MOLECULE TYPE: peptide (xi) SEQUENCE DESCRIPTION: SEQ ID NO:36:

```
    Trp  Cys  Tyr  Arg  Lys  Cys  Phe  Lys  Gly  Phe  Cys  Tyr  Arg  Lys  Cys  Arg
    1              5                        10                       15
```

(2) INFORMATION FOR SEQ ID NO:37:

(i) SEQUENCE CHARACTERISTICS:
       (A) LENGTH: 16 amino acids
       (B) TYPE: amino acid
       (C) STRANDEDNESS: single
       (D) TOPOLOGY: unknown (ii) MOLECULE TYPE: peptide (xi) SEQUENCE DESCRIPTION: SEQ ID NO:37:

```
    Trp  Cys  Tyr  Arg  Lys  Cys  Tyr  Arg  Gly  Phe  Cys  Tyr  Arg  Lys  Cys  Arg
    1              5                        10                       15
```

(2) INFORMATION FOR SEQ ID NO:38:

(i) SEQUENCE CHARACTERISTICS:
       (A) LENGTH: 16 amino acids
       (B) TYPE: amino acid
       (C) STRANDEDNESS: single
       (D) TOPOLOGY: unknown (ii) MOLECULE TYPE: peptide (xi) SEQUENCE DESCRIPTION: SEQ ID NO:38:

```
    Trp  Cys  Tyr  Arg  Lys  Cys  Tyr  Arg  Gly  Tyr  Cys  Tyr  Arg  Lys  Cys  Arg
    1              5                        10                       15
```

(2) INFORMATION FOR SEQ ID NO:39:

(i) SEQUENCE CHARACTERISTICS:
       (A) LENGTH: 18 amino acids
       (B) TYPE: amino acid
       (C) STRANDEDNESS: single
       (D) TOPOLOGY: unknown (ii) MOLECULE TYPE: peptide (xi) SEQUENCE DESCRIPTION: SEQ ID NO:39:

```
    Arg  Arg  Trp  Cys  Tyr  Arg  Lys  Cys  Tyr  Arg  Gly  Phe  Cys  Tyr  Arg  Lys
    1              5                        10                       15

Cys  Arg
```

POLYPEPTIDES WITH AFFINITY TO LIPOPOLYSACCHARIDES AND THEIR USES

1. FIELD OF THE INVENTION

This invention relates to a novel polypeptide(s) or a pharmaceutically acceptable salt thereof exhibiting a strong affinity to lipopolysaccharides, particularly endotoxins. The polypeptide may be used in a pharmaceutical composition as an anti-bacterial or anti-viral agent (e.g. anti-HIV agent). This application is a Continuation-In-Part of the earlier filed, co-pending PCT Application PCT/JP91/01201, filed Sep. 11, 1991, which designated the United States and which entered national phase examination in the United States Patent Office Jul. 1, 1992 as Application Ser. No. 07/856,026, entitled "Novel Polypeptide and Anti-HIV Drug Prepared Therefrom" by Nobutaka Fujii and Naoki Yamamato.

2. BACKGROUND OF THE INVENTION

Two families of antimicrobial polypeptides have been isolated from horseshoe crabs (see, for example, Shigenaga, 1990, J. Biol. Chem. 265:21350–21354; Kawano et al., 1990, J. Biol. Chem. 265:15365–15367; Muta et al., 1990, J. Biochem. 108:261–266; Japanese Laid-Open Patent Publication No. 167230/1990; Japanese Laid-Open Patent Publication No. 152987/1990; Japanese Laid-Open Patent Publication No. 53799/1990; Published Searched Application 500194/1990; Miyata et al., 1989, J. Biochem. 106:663–668; Akaji et al., 1989, Chem. Pharm. Bull. 37:2661–2664; Taisha (Metabolism) 26:301–311 (1989); Shieh et al., 1989, FEBS Lett. 252:121–124; and Nakamura et al., 1988, J. Biol. Chem. 263:16709–16713). One family, the tachyplesin family has been isolated from the Japanese horseshoe crab Tachypleus. Three tachyplesins, I, II, and III have been identified; their amino acid sequences are shown in FIG. 1. Additionally, a tachyplesin peptide derivative with a carboxyl-terminal extension of glycyl lysine has been found in a Southeast Asian horseshoe crab species, *carcinoscorpius rotundicauda* (Muta et al., 1990, J. Biochem. 108:261–266). A second family, the polyphemusin family has been isolated from the hemocytes of the American horseshoe crab, Limulus Polyphemus. Two polyphemusins, I and II have been identified; their amino acid sequences are also shown in FIG. 1. The polypeptides in both families consist of 17 or 18 amino acid residues and have four conserved regions in common and two disulfide bridges (see FIG. 1). Both tachyplesins and polyphemusins have been found to inhibit the growth of both Gram-negative and -positive bacteria at low concentrations as well as fungi, such as *Candida albicans* and form complexes with bacterial lipopolysaccharides (Shigenaga et al., 1990, J. Biol. Chem. 265:21350–21354 and Muta et al., 1990, J. Biochem. 108:261–266). Also, the polypeptides in a tachyplesin family have been found to exhibit some inhibition activity for virus, such as Influenza virus, vesicular stomatitis virus (Murakami et al., 1991, Chemotherapy 37:327–334) or human immunodeficiency virus (Morimoto, et al., 1991, Chemotherapy 37:206–211).

3. SUMMARY OF THE INVENTION

The present invention relates to a novel polypeptide(s) which is derived from and possesses some homology to the high endotoxin affinity polypeptides of horseshoe crabs, specifically, tachyplesins and polyphemusins, but have a significant difference. In the horseshoe crab polypeptides, the amino acid at the 6-position for tachyplesins or 7-position for polyphemusins is a valine (Val), a neutral aliphatic amino acid. In the polypeptide(s) of the present invention, the amino acid residue at the 6-position is a lysine (Lys) or arginine (Arg) residue; these are basic amino acid residues having substantially different properties from the valine residue. Moreover, the amino acid residue at the 11-position in the polypeptides of the present invention is a tyrosine (Tyr), phenylalanine (Phe) or tryptophan (Trp), an aromatic amino acid residue having different properties from the isoleucine (Ile) at the 11-position of tachyplesins.

The novel polypeptides of the present invention may be used as an anti-HIV agent. As will be detailed in the Section 6, infra, the polypeptide(s) of the invention have anti-HIV activity values that are significantly higher than known high endotoxin affinity polypeptides of horseshoe crabs.

3.1 DEFINITIONS

Peptide sequences defined herein are represented by three letter abbreviations for amino acid residues as follows:

Ala (alanine); Arg (arginine); Cys (cysteine); Gly (glycine); Ile (isoleucine); Leu (leucine); Lys (lysine); Phe (phenylalanine); Trp (tryptophan); Tyr (tyrosine); and Val (valine).

The following terms, as used herein, will have the meanings indicated:

HIV = human immunodeficiency virus (all variants)
MOI = multiplicity of infection
SI = selectivity index (ratio of $CC_{50}$ to $EC_{50}$)

4. BRIEF DESCRIPTION OF THE DRAWINGS

FIG. 1 shows the amino acid sequences of Tachyplesin I (SEQ. ID NO: 1), Tachyplesin II (SEQ. ID NO: 2, Tachyplesin III (SEQ. ID NO: 3), Polyphemusin I (SEQ. ID NO: 4), and Polyphemusin II (SEQ. ID NO: 5). Conserved amino acids are boxed. The disulfide linkages between Cys-3 or -4 and -16 or -17 and Cys-7 or -8 and -12 are shown by solid lines.

Figure 2:
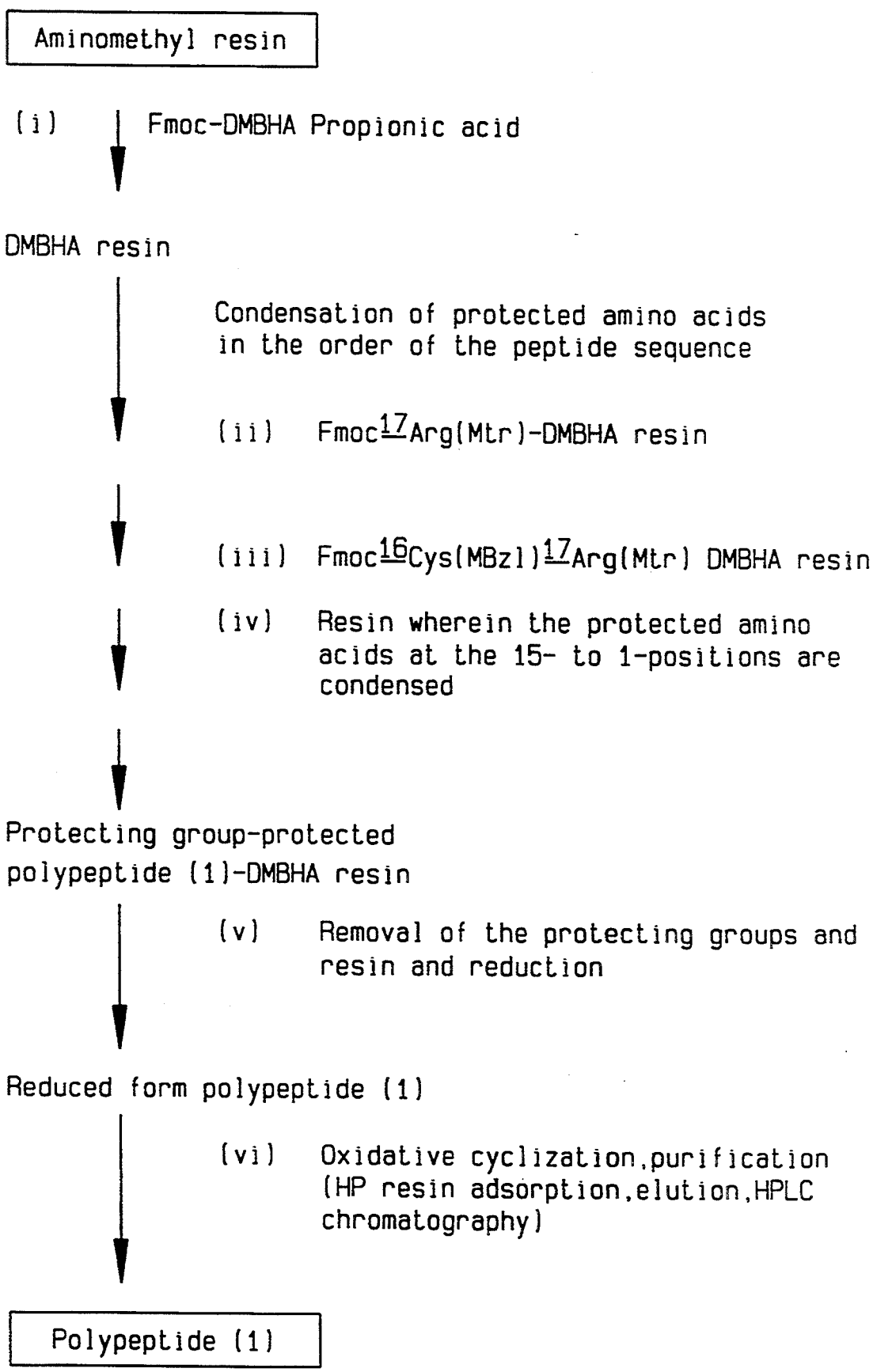

FIG. 2 shows a synthetic scheme for synthesizing polypeptide (1) of the invention.

5. DETAILED DESCRIPTION OF THE INVENTION

The invention relates to a novel polypeptide represented by the following formula (I) (SEQ. ID NO: 6)

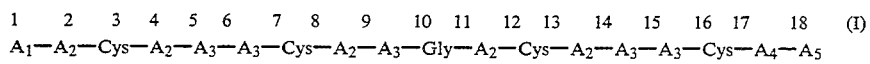

$$A_1-A_2-Cys-A_2-A_3-A_3-Cys-A_2-A_3-Gly-A_2-Cys-A_2-A_3-A_3-Cys-A_4-A_5 \quad (I)$$

positions 1 2 3 4 5 6 7 8 9 10 11 12 13 14 15 16 17 18 or salt thereof in which $A_1$ is a hydrogen or at least one and no more than two amino acids selected from the group consisting of lysine and arginine, $A_2$ is a tyrosine, phenylalanine or tryptophan residue, $A_3$ is an arginine or lysine residue, A₄ is at least one and no more than two amino acids selected from the group consisting of lysine and arginine, A₅ is an —OH (derived from the carboxylic group) or an —NH₂ (derived from the acid amide group)

Cys is a cysteine residue, and

Gly is a glycine residue.

In a specific embodiment, the cysteine residues at the 3- and 16-positions and/or the cysteine residues at the 7- and 12-positions may be linked through a disulfide linkage (-S-S-).

Specific examples of the polypeptides of the invention represented by the formula (I), are shown in Table I and are numbered (1) to (33). Each symbol denotes the corresponding amino acid residue by the internationally admitted three-letter expression (see Section 3.1., Supra).

TABLE I

| | 1' | 1 | 2 | 3 | 4 | 5 | 6 | 7 | 8 | 9 | 10 | 11 | 12 | 13 | 14 | 15 | 16 | 17 | 17' | 18 |
|---|---|---|---|---|---|---|---|---|---|---|---|---|---|---|---|---|---|---|---|---|
| (1) (SEQ ID NO: 7) | Arg | Arg | Trp | Cys | Tyr | Arg | Lys | Cys | Tyr | Lys | Gly | Tyr | Cys | Tyr | Arg | Lys | Cys | Arg | | —NH₂ |
| (2) (SEQ ID NO: 8) | Arg | Arg | Trp | Cys | Tyr | Arg | Lys | Cys | Tyr | Lys | Gly | Tyr | Cys | Tyr | Arg | Lys | Cys | Arg | Arg | —NH₂ |
| (3) (SEQ ID NO: 9) | | Arg | Trp | Cys | Tyr | Arg | Lys | Cys | Tyr | Lys | Gly | Phe | Cys | Tyr | Arg | Lys | Cys | Arg | | —NH₂ |
| (4) (SEQ ID NO: 10) | | Arg | Trp | Cys | Tyr | Arg | Lys | Cys | Tyr | Lys | Gly | Phe | Cys | Tyr | Arg | Lys | Cys | Arg | Arg | —NH₂ |
| (5) (SEQ ID NO: 11) | Arg | Arg | Trp | Cys | Trp | Arg | Lys | Cys | Tyr | Lys | Gly | Tyr | Cys | Trp | Arg | Lys | Cys | Arg | | —NH₂ |
| (6) (SEQ ID NO: 12) | Arg | Arg | Trp | Cys | Trp | Arg | Lys | Cys | Trp | Lys | Gly | Trp | Cys | Trp | Arg | Lys | Cys | Arg | | —NH₂ |
| (7) (SEQ ID NO: 13) | Arg | Arg | Tyr | Cys | Tyr | Arg | Lys | Cys | Tyr | Lys | Gly | Tyr | Cys | Trp | Arg | Lys | Cys | Arg | | —NH₂ |
| (8) (SEQ ID NO: 14) | Arg | Arg | Tyr | Cys | Tyr | Arg | Lys | Cys | Tyr | Lys | Gly | Tyr | Cys | Tyr | Arg | Lys | Cys | Arg | Arg | —NH₂ |
| (9) (SEQ ID NO: 15) | Arg | Arg | Trp | Cys | Tyr | Lys | Lys | Cys | Tyr | Lys | Gly | Tyr | Cys | Tyr | Lys | Lys | Cys | Arg | | —NH₂ |
| (10) (SEQ ID NO: 16) | Lys | Lys | Trp | Cys | Tyr | Lys | Lys | Cys | Tyr | Lys | Gly | Tyr | Cys | Tyr | Lys | Lys | Cys | Lys | | —NH₂ |
| (11) (SEQ ID NO: 17) | Lys | Lys | Trp | Cys | Tyr | Lys | Lys | Cys | Tyr | Lys | Gly | Tyr | Cys | Tyr | Lys | Lys | Cys | Lys | Lys | —NH₂ |
| (12) (SEQ ID NO: 18) | Arg | Arg | Trp | Cys | Tyr | Lys | Arg | Cys | Tyr | Lys | Gly | Tyr | Cys | Tyr | Lys | Arg | Cys | Arg | | —NH₂ |
| (13) (SEQ ID NO: 19) | Arg | Arg | Trp | Cys | Tyr | Arg | Lys | Cys | Tyr | Lys | Gly | Phe | Cys | Tyr | Arg | Lys | Cys | Arg | | —NH₂ |
| (14) (SEQ ID NO: 20) | Arg | Arg | Trp | Cys | Tyr | Arg | Lys | Cys | Tyr | Arg | Gly | Tyr | Cys | Tyr | Arg | Lys | Cys | Arg | | —NH₂ |
| (15) (SEQ ID NO: 21) | | Arg | Trp | Cys | Tyr | Arg | Lys | Cys | Tyr | Arg | Gly | Tyr | Cys | Tyr | Arg | Lys | Cys | Arg | | —NH₂ |
| (16) (SEQ ID NO: 22) | Arg | Arg | Trp | Cys | Tyr | Arg | Lys | Cys | Phe | Arg | Gly | Phe | Cys | Tyr | Arg | Lys | Cys | Arg | | —NH₂ |
| (17) (SEQ ID NO: 23) | | Arg | Trp | Cys | Tyr | Arg | Lys | Cys | Phe | Arg | Gly | Phe | Cys | Tyr | Arg | Lys | Cys | Arg | | —NH₂ |
| (18) (SEQ ID NO: 24) | Arg | Arg | Trp | Cys | Tyr | Lys | Arg | Cys | Tyr | Arg | Gly | Phe | Cys | Tyr | Lys | Arg | Cys | Arg | | —NH₂ |
| (19) (SEQ ID NO: 25) | | Arg | Trp | Cys | Tyr | Arg | Lys | Cys | Tyr | Arg | Gly | Phe | Cys | Tyr | Arg | Lys | Cys | Arg | | —NH₂ |
| (20) (SEQ ID NO: 26) | Arg | Arg | Trp | Cys | Tyr | Arg | Lys | Cys | Phe | Lys | Gly | Phe | Cys | Tyr | Arg | Lys | Cys | Arg | | —NH₂ |
| (21) (SEQ ID NO: 27) | | Arg | Trp | Cys | Tyr | Arg | Lys | Cys | Phe | Lys | Gly | Phe | Cys | Tyr | Arg | Lys | Cys | Arg | | —NH₂ |
| (22) (SEQ ID NO: 28) | Arg | Arg | Trp | Cys | Tyr | Arg | Lys | Cys | Phe | Lys | Gly | Phe | Cys | Tyr | Arg | Lys | Cys | Arg | Arg | —NH₂ |
| (23) (SEQ ID NO: 29) | Arg | Arg | Trp | Cys | Tyr | Lys | Arg | Cys | Phe | Lys | Gly | Phe | Cys | Tyr | Lys | Arg | Cys | Arg | | —NH₂ |

TABLE I-continued

| | | |
|---|---|---|
| (24) (SEQ ID NO: 30) | Arg—Arg—Trp—Cys—Tyr—Lys—Arg—Cys—Tyr—Arg—Gly—Tyr—Cys—Tyr—Lys—Arg—Cys—Arg | —NH$_2$ |
| (25) (SEQ ID NO: 31) | Arg—Arg—Trp—Cys—Tyr—Arg—Arg—Cys—Tyr—Lys—Gly—Tyr—Cys—Tyr—Arg—Arg—Cys—Arg | —NH$_2$ |
| (26) (SEQ ID NO: 32) | Arg—Trp—Cys—Tyr—Arg—Lys—Cys—Tyr—Lys—Gly—Tyr—Cys—Tyr—Arg—Lys—Cys—Arg | —NH$_2$ |
| (27) (SEQ ID NO: 33) | Trp—Cys—Tyr—Arg—Lys—Cys—Tyr—Lys—Gly—Tyr—Cys—Tyr—Arg—Lys—Cys—Arg | —NH$_2$ |
| (28) (SEQ ID NO: 34) | Trp—Cys—Tyr—Arg—Lys—Cys—Tyr—Lys—Gly—Phe—Cys—Tyr—Arg—Lys—Cys—Arg | —NH$_2$ |
| (29) (SEQ ID NO: 35) | Trp—Cys—Tyr—Arg—Lys—Cys—Phe—Arg—Gly—Phe—Cys—Tyr—Arg—Lys—Cys—Arg | —NH$_2$ |
| (30) (SEQ ID NO: 36) | Trp—Cys—Tyr—Arg—Lys—Cys—Phe—Lys—Gly—Phe—Cys—Tyr—Arg—Lys—Cys—Arg | —NH$_2$ |
| (31) (SEQ ID NO: 37) | Trp—Cys—Try—Arg—Lys—Cys—Tyr—Arg—Gly—Phe—Cys—Tyr—Arg—Lys—Cys—Arg | —NH$_2$ |
| (32) (SEQ ID NO: 38) | Trp—Cys—Tyr—Arg—Lys—Cys—Tyr—Arg—Gly—Tyr—Cys—Tyr—Arg—Lys—Cys—Arg | —NH$_2$ |
| (33) (SEQ ID NO: 39) | Arg—Arg—Trp—Cys—Tyr—Arg—Lys—Cys—Tyr—Arg—Gly—Phe—Cys—Tyr—Arg—Lys—Cys—Arg | —NH$_2$ |

Like the high endotoxin affinity polypeptides isolated from horseshoe crabs known in the art, the polypeptides of the present invention have an antiparallel beta-sheet structure due to the existence of intramolecular hydrogen bondings and four cysteine residues at the 3-, 7-, 12-, and 16-positions. The turning position with possibly beta-turn structure is located at the 9- and 10-positions. The peptide part of the 3-position to the 8-position and the peptide part of the 11-position to the 16-position face each other.

However, in contrast to the known polypeptides isolated from horseshoe crabs, the polypeptide(s) of the present invention are more basic. Specifically, the amino acid residue at the 6-position is an arginine (Arg) or lysine (Lys) residue. The amino acid residue at the 6-position in polypeptides isolated from horseshoe crabs is a valine residue.

Due to their basic nature, the polypeptide(s) of the present invention may form a salt by acid addition. For example, the polypeptide forms a salt with an inorganic acid (hydrochloric acid, hydrobromic acid, phosphoric acid, nitric acid, sulfuric acid or the like) or an organic carboxylic acid (acetic acid, halo acetic acid such as trifluoroacetic acid, propionic acid, maleic acid, succinic acid, malic acid, citric acid, tartaric acid, salicylic acid and uronic acid such as glucuronic acid or hyaluronic acid or the like) or an organic sulfonic acid (methanesulfonic acid, p-toluenesulfonic acid or the like) including sulfonic acid sugar ester such as chondroitin sulfates.

5.1 PREPARATION OF POLYPEPTIDES

The novel polypeptide of the invention can be prepared by methods known in the art, for example, solid phase synthesis techniques described in "Solid-Phase Peptide Synthesis" Stewart & Young, Pierce chemical Company, Rockford, Ill. (1984). Namely, a straight chain polypeptide of the invention having the above formula (I) (SEQ. ID NO: 9) can be obtained by linking the carboxyl group of an N-protected arginine at the 17-position to an insoluble resin having amino groups directly attached or alternatively attached through a spacer having a functional group capable of linking to a carboxyl group (e.g. one capable of converting the carboxyl group of arginine to a p-carboxymethylbenzylester). The amino group of the insoluble resin having the arginine (Arg) residue at the 17-position after de-blocking the α-amino($N_\alpha$)-protecting group is capable of successively linking, according to the solid phase method, with the respective protected amino acids of the 16-position to the 1-position of the amino acid sequence represented by the following formula (I) (SEQ ID NO: 6)

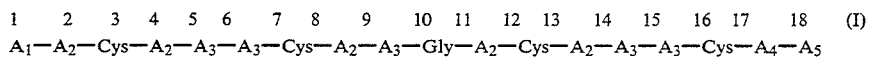

$$\overset{1}{A_1}—\overset{2}{A_2}—\overset{3}{Cys}—\overset{4}{A_2}—\overset{5}{A_3}—\overset{6}{A_3}—\overset{7}{Cys}—\overset{8}{A_2}—\overset{9}{A_3}—\overset{10}{Gly}—\overset{11}{A_2}—\overset{12}{Cys}—\overset{13}{A_2}—\overset{14}{A_3}—\overset{15}{A_3}—\overset{16}{Cys}—\overset{17}{A_4}—\overset{18}{A_5} \qquad (I)$$

[wherein $A_1$, $A_2$, $A_3$, $A_4$, $A_5$, Cys and Gly, are as defined in the above formula (I)], and then eliminating (removing) the insoluble resin and the protecting groups of the amino acids. In this instance, the carboxyl terminus of the amino acid residue at the 17-position can be either free ($A_5$ corresponds to —OH) or converted to an acid amide ($A_5$ corresponds to —NH$_2$). The two cysteines at the 3- and 16-positions and the 7- and 12-positions can form a disulfide linkage (-S-S-) through the mercapto groups by air oxidation, or either disulfide linkage can be formed according to the method of Atherton, E., et al., 1985, J. Chem. Soc., Perkin Trans. 1:2065, namely through steps of selectively protecting the mercapto groups of either pair of cysteines at the 3- and 16-positions and the 7- and 12-positions with the protecting group, t-BuS (t-butylthio) and the mercapto groups of the other pair of cysteines with the protecting group, Acm (acetamidomethyl); removing the t-BuS, partially oxidizing the mercapto groups; and then removing the Acm protecting group using procedures known in the art.

Any insoluble resin having an amino group can be used in synthesizing the novel polypeptide of the invention, as long as it can link through its amino groups to the carboxyl group of the N-protected arginine or lysine at the C-terminus or in some cases to the carboxyl group of the spacer linked thereto and thereafter can be eliminated (removed). Examples of such insoluble resins include but are not limited to amino-methyl resins (aminomethylated styrene-divinylbenzene copolymers), benzhydrylamine resins, methylbenzhydrylamine resins and aminomethylphenoxymethyl resins and derivatives thereof. When a benzhydrylamine resin, methylbenzhydrylamine resin, dimethoxybenzhydrylamine (DMBHA) resin or aminomethylphenoxymethyl resin is used, an amide is directly obtained by cleavage, but an amino-methyl resin is preferred in view of yield.

Respective amino acids to be used in the solid phase synthetic method can be L-forms or D-forms. The protected amino acid is an amino acid whose functional groups may be protected with a protecting group using procedures known in the art, or various protected amino acids may be purchased commercially. Those skilled in the art will recognize that polypeptide synthetic methods require the use of a protecting group to stabilize a labile side chain of an amino acid to prevent the side chain from being chemically altered during the synthesis process. A protecting group for the α-amino group of an amino acid is selected from the group including but not limited to Boc (t-butyloxycarbonyl) or Fmoc (9-fluorenylmethyloxycarbonyl). A protecting group for the guanidino group of arginine (Arg) is selected from the group including but not limited to Tos (tosyl), NO₂ (nitro), Mtr (4-methoxy-2,3,6-trimethylbenzene-sulfonyl) or Pmc (2,2,5,7,8-pentamethyl- chroman-6-sulfonyl). A protecting group for the mercapto group of cysteine (Cys) may be selected from the group including but not limited to Bzl (benzyl), MBzl (4-methoxybenzyl), 4-MeBzl (4-methylbenzyl) , Acm (acetamidomethyl), Trt (trityl), Npys (3-nitro-2-pyridinesulfenyl ) , t-Bu (t-butyl) or t-BuS (t-butylthio), and Mbzl, 4-MeBzl, Trt, Acm and Npys are preferred. A protecting group for the hydroxyl group of tyrosine (Tyr) is selected from the group including but not limited to Bzl, Cl₂Bzl (2,6-dichlorobenzyl) or t-Bu. A protecting group for the ε-amino group of lysine (Lys) is selected from the group including but not limited to Z (benzyloxycarbonyl), ClZ (2-chlorobenzyloxycarbonyl), Boc or Npys.

The coupling of protected amino acids can be carried out according to condensation methods known in the art, such as, for example, a DCC (dicyclohexylcarbodiimide) method, DIPCDI (diisopropylcarbodiimide) method [Tartar, A. et al., 1979, J. Org. Chem. 44:5000], active ester method, mixed or symmetrical acid anhydride method, carbonyldiimidazole method, DCC-HOBt (1-hydroxybenzotriazole) method [König W. et al., 1970, Chem. Ber., 103, 788, 2024, 2034,] or diphenylphosphoryl azide method, but preferably using the DCC method, DCC-HOBt method, DIPCDI-HOBt method or symmetrical acid anhydride method. The condensation reaction may be carried out in an organic solvent such as dichloromethane or dimethylformamide or a mixed solvent thereof. A deblocking reagent such as trifluoroacetic acid/dichloromethane, HCl/dioxane, piperidine/dimethylformamide (DMF) is used to deblock the protecting group for an α-amino group. The degree of the progress of condensation reaction in each step of synthesis is pursued by the method of E. Kaiser et al. [Anal. Biochem., 34, 595 (1970)) (the ninhydrin reaction method).

When an aminomethyl resin derivative is used as the insoluble resin, the protected polypeptide can be removed from the resin, for example, by treating the protected peptide resin with ammonia in an appropriate solvent. The resulting protected peptide is then treated with hydrogen fluoride to obtain a polypeptide amide represented by the above formula and freed of all the protecting groups. When a benzhydrylamine resin, methylbenzhydrylamine resin, aminomethylphenoxymethyl resin or DMBHA resin [Funakoshi, S. et al., 1988, J. Chem. Soc., Chem. Commun. 382] is used as the insoluble resin, the polypeptide may be removed from the resin and the protecting groups can simultaneously be removed from the polypeptide by treating the protected peptide resin with hydrogen fluoride, TFMSA (trifluoromethanesulfonic acid) [published by Academic Press, edited by E. Gross; Yajima, H. et al.; "The Peptides" vol. 5, page 65 (1983)], TMSOTf (trimethylsilyl triflate) [Fujii, N. et al.; J. Chem. Soc., Chem. Commun., 1987, 274] or TMSBr (trimethylsilyl bromide) [Fujii, N. et al.; Chem. Pharm. Bull., 35, 3880 (1987)] or the like.

In a preferred embodiment, the resulting polypeptide is reduced with 2-mercaptoethanol, DTT (dithiothreitol) or the like to make sure the mercapto groups of the cysteines are in reduced form. The mercapto groups may be subsequently oxidized to obtain a cyclic polypeptide. The oxidation treatment can be carried out by a known method. Usually, such oxidizing agent as air or a ferricyanate (e.g. potassium ferricyanide) is used.

Alternatively, the polypeptide(s) of the invention may be produced using recombinant DNA technology. Accordingly, the nucleotide coding sequences for the polypeptide(s) of the invention may be cloned and expressed using techniques well known in the art. See, for example, Maniatis et al., Molecular Cloning, A Laboratory Manual, Cold Spring Harbor Laboratory, Cold Spring Harbor, N.Y., 1991.

The polypeptide(s) of the invention can be isolated and purified by means known in the art for polypeptides, for example, extraction, recrystallization, various chromatographies (gel filtration, ion exchange, partition, adsorption, reverse-phase), electrophoresis, countercurrent distribution, etc., and reverse-phase high performance liquid chromatography is the most effective.

5.2 USES FOR POLYPEPTIDES

The polypeptide(s) of the invention represented by the formula (I) have an ability to bind to endotoxins, an antibacterial activity, and an activity to hemolyze endotoxin-sensitized hemocytes. Additionally, the polypeptide(s) of the invention possess an antiviral activity. In a specific embodiment, the polypeptide(s) of the invention have anti-HIV activity. As will be detailed in Section 6, infra, the polypeptides of the invention exhibit significantly higher anti-HIV activity than known high endotoxin affinity polypeptides (e.g., Tachyplesins I, II or III or Polyphemusins I or II) exhibits.

The polypeptide(s) of the present invention therefore may be used in a pharmaceutical composition comprising the polypeptide(s) of the invention or salt thereof and a pharmaceutically acceptable carrier selected in accordance with the administration method and administration form of the pharmaceutical composition. The pharmaceutical carriers may be such physiologically compatible buffers as Hank's or Ringer's solution, physiological saline, a mixture consisting of saline and glucose, and heparinized sodium-citrate-citric acid dextrose solution. The pharmaceutical composition is orally or parenterally administered in accordance with the object of treatment, and can be prepared as a preparation such as powder, granules, a solution for injection or oral administration, tablets, suppositories, pessaries, ointment, cream or aerosol, using appropriate pharmaceutical carriers in accordance with the administration method.

When the pharmaceutical composition is directly administered as an injection to a patient, the polypeptide or its salt of the invention can continuously or intermittently administered in an amount of 10 to 5,000 mg per kg of human body weight and per one day and by intravenous drip as a solution in physiological saline.

6. EXAMPLES

In the examples herein, the synthesis of polypeptide (1) is described. Additionally, the results of anti-HIV activity assays for the polypeptides of the invention and known high endotoxin affinity polypeptides are disclosed. Polypeptides of the invention have a significantly higher anti-HIV activity than known high endotoxin affinity polypeptides.

Apparatuses and reagents used in the following examples are as follows:
HPLC apparatus: Waters Co. (USA) Model 600
Column of the apparatus:
Asahipak ODP-90
(Asahi Chemical Industry Co., Ltd.)
Fmoc amino acid: produced by
Kokusan Kagaku Co., Ltd.
Amino resin and condensing agent: produced by
Peptide Kenkyusho Co., Ltd.
FAB-MS (FAB-mass spectrograph):
VC Co. (USA), Model ZAB-SE

6.1. EXAMPLE 1: SYNTHESIS OF THE POLYPEPTIDE (1)

The synthesis of a polypeptide (1) (SEQ. ID NO: 7) which has the formula shown below is described in Sections 6.1.1–6.1.7, infra. Polypeptides (2–33) (SEQ. ID NOS: 8–39) (see Table I, supra for structures) are synthesized using similar procedures.

6.1.1. INTRODUCTION INTO AN AMINOMETHYL RESIN OF Fmoc-DMBHA-CH₂CH₂COOH
[(3-(α-Fmoc-amino-4-methoxybenzyl) 4-methoxyphenyl) propionic acid 270 mg (0.2 mmole) of an aminomethyl resin (0.74 meq/g) and 268.5 mg (0.5 mmole, 2.5 eq) of Fmoc-DMBHA-CH₂CH₂COOH (MW 537) were placed in a solid phase synthesizing column, and the condensation reaction was carried out for 2 hours by the method of DIPCDI-HOBT in DMF according to the method of Guo, L. et al. [Chem. Pharm. Bull., 36, 4989 (1988)].

After the completion of the condensation reaction, coupling was carried out for the protection of the free amino groups using acetic anhydride (DMBHA resin).

6.1.2. INTRODUCTION OF ARGININE AT THE 17-POSITION INTO THE DMBHA RESIN

After removing the Fmoc groups from the DMBHA resin prepared in Section 6.1.1., Supra, with 20% piperidine/DMF, 2.5 equivalents (eq) of Fmoc-Arg(Mtr)-OH based on the DMBHA resin was added, and the condensation reaction was carried out in DMF according to the DIPCDI-HOBt method.

The degree of progress of the condensation reaction was pursued by measurement according to the ninhydrin test of Kaiser, E. et. al. [Anal. Biochem., 34, 595 (1970)].

6.1.3. INTRODUCTION OF CYSTEINE AT THE 16-POSITION

After the removal of the Fmoc groups from the DMBHA resin with 20% piperidine/DMF, 2.5 eq of Fmoc-Cys (MBzl)-OH based on the DMBHA resin was added, and condensation reaction was carried out in DMF by the method of DIPCDI-HOBt. The degree of progress of the condensation reaction was pursued similarly to 6.1.2., supra by measurement according to the ninhydrin test.

6.1.4. INTRODUCTION OF AMINO ACIDS FROM THE 15-TO 1-POSITIONS

Likewise as above, Lys(Boc), Arg(Mtr), Tyr(t-Bu), Cys(MBzl), Tyr(t-Bu), Gly, Lys(Boc), Tyr(t-Bu), Cys(MBzl), Lys(Boc), Arg(Mtr), Tyr(t-Bu), Cys

```
 1    2    3   4   5   6   7   8   9   10  11  12        (1)
Arg—Arg—Trp—Cys—Tyr—Arg—Lys—Cys—Tyr—Lys—Gly—Tyr—Cys—

13  14  15  16  17  18
Tyr—Arg—Lys—Cys—Arg—NH₂
```

The Cys residues at the 3- and 16-positions and at the 7- and 12-positions are linked respectively through disulfide linkage.

(MBzl), Trp, Arg (Mtr) and Arg (Mtr) were successively introduced into the DMBHA resin to obtain a protecting group-protected peptide (1) resin.

Each amino acid condensation reaction in the solid phase synthesis was carried out according to the operation conditions of the Table II.

TABLE II

| Operation | Reagent | Solvent | Time × Repeat number |
|---|---|---|---|
| Removal of Fmoc Group | 20% piperidine/DMF | DMF | 5 minutes × 3 |
| Washing | — | DMF | 1 minute × 6 |
| Condensation reaction | Fmoc amino acid (2.5 eq) + DIPCDI + HOBt | DMF | 2 hours × 1 |

TABLE II-continued

| Operation | Reagent | Solvent | Time × Repeat number |
|---|---|---|---|
| Washing | — | DMF | 1 minutes × 4 |

6.1.5. PREPARATION OF THE POLYPEPTIDE (1) BY THE REMOVAL OF THE PROTECTING GROUPS, REMOVAL OF POLYPEPTIDE (1) FROM THE RESIN AND PARTIAL PURIFICATION

The protected polypeptide (1) resin was subjected to 20% piperidine/DMF treatment to remove the Fmoc group, and then subjected to reaction at 25° C. for 2 hours in a 1M TMSOTf-thioanisole/TFA (trifluoroacetic acid) system (10 ml of trifluoroacetic acid in the presence of m-cresol (100 eq) and ethanedithiol (300 eq) per 100 mg of the resin. The resin was filtered off from the reaction mixture and washed twice with 1 ml of trifluoroacetic acid. 100 ml of ice-cooled dry ether was subsequently added to mixture of the filtrate and the washing. The formed precipitate was centrifuged, and the residue was separated from the supernatant by decantation. The resulting residue was washed with cold ether, dissolved in 10 ml of 4N ACOH, 830 mg, 80 eq of dithiothreitol was added and the mixture was stirred at room temperature overnight.

The reaction solution was centrifuged, the supernatant was treated with Sephadex G-10 (3.7×5 cm), gel filtered with 4N acetic acid (AcOH), and the flow-through was collected as the main eluate part and lyophilized to obtain as powder, a partially purified non-cyclized polypeptide (1).

6.1.6. PREPARATION OF THE POLYPEPTIDE (1) BY AIR OXIDATION

A half amount of the flow-through fraction was adjusted to pH 7.5 with concentrated aqueous ammonia, and subjected to air oxidation by aeration to carry out the cyclization reaction. After the completion of air oxidation, the cyclized polypeptide (1) was adsorbed onto 10 g of Diaion HP-20 resin, and subsequently eluted with 60% $CH_3CN$ (in 1N ACOH). The eluate was concentrated at room temperature under reduced pressure to remove $CH_3CN$ and then lyophilized to give powder. The powder was dissolved in a small amount of water, and the solution was poured on an Asahipak and purified by high performance liquid chromatography (HPLC-Model 600 produced by Waters Co.) using gradient elution with $CH_3CN$ to obtain the polypeptide (1) of a single peak in a yield of 27% (a value calculated based on the protecting group-protected polypeptide (1) resin).

6.1.7. ANALYSIS OF THE POLYPEPTIDE

The amino acid composition value was determined by leucine aminopeptidase digestion of the polypeptide purified as in Section 6.1.6., Supra and was found to be well within the calculated value of the composition based on the amino acid sequence of the formula (1).

The specific rotation $[\alpha]_D^{20}$ the obtained polypeptide was +8.4° (C=0.1, 1N acetic acid).

6.2. EXAMPLE 2: ANTIVIRAL ACTIVITY AGAINST HUMAN IMMUNODEFICIENCY VIRUS (HIV)

The antiviral activity against HIV of the polypeptide (1) synthesized in Example 1 as well as polypeptides (2), (3), (4), (7), (12), (13), (14), (20), (21) and (26) was tested and evaluated according to the following method.

HIV-infected MT-4 cells ($2.5 \times 10_4$ cells/well, multiplicity of infection (MOI): 0.001) immediately after infection were added together with the test substance with various changes of the concentration to a 96-well microtitre plate. After incubation at 37° C. for 5 days in a $CO_2$ incubator, the number of survivor cells was measured by the MTT method [Pauwels et al.; J. Virol. Methods, 20, 309–321 (1988)]. The antiviral activity is expressed as a concentration at which cell death due to HIV infection is 50% inhibited ($EC_{50}$: 50% effective concentration). On the other hand, in order to know the cytotoxicity of the test substance on the MT-4 cells, virus-noninfected cells are incubated, likewise as above, together with the test compound with various changes of the concentration. The cytotoxicity is expressed as 50% cytotoxic concentration ($EC_{50}$) due to the test substance. Further, the rough ratio of $CC_{50}$ to $EC_{50}$ ($CC_{50}/EC_{50}$) is expressed as an effective ratio (SI=-selectivity index).

Table III shows the $EC_{50}$ $CC_{50}$ and SI values of polypeptides (1) (SEQ. ID NO: 7), (2) (SEQ. ID NO: 8), (3) (SEQ. ID NO: 9), (4) (SEQ. ID NO: 10), (7) (SEQ. ID NO: 13), (12) (SEQ. ID NO: 18), (13) (SEQ. ID NO: 19), (14) (SEQ ID NO: 20), (20) (SEQ. ID NO: 26), (21) (SEQ. ID NO: 27) and (26) (SEQ. ID NO: 32) and known polypeptides having a high affinity to endotoxins, specifically, Tachyplesin I and II (SEQ. ID NOS: 1–2) and Polyphemusin I and II (SEQ. ID NOS: 4–5) and known Anti-HIV agent AZT.

Table IV shows the physical properties of polypepides (1) (SEQ. ID NO: 7), (3) (SEQ. ID NO: 9), (13) (SEQ. ID NO: 19), (20) (SEQ. ID NO: 26) and (21) (SEQ. ID NO: 27).

TABLE III

| Compound Type | Compound Name | Compound Structure 1' 1 2 3 4 5 6 7 8 9 10 11 12 13 14 15 16 17 17' 18 | CC₅₀ *1 | Anti-HIV Activity EC₅₀ *2 | SI *3 |
|---|---|---|---|---|---|
| Synthesized polypeptides of the invention | (1) | Arg—Arg—Trp—Cys—Tyr—Arg—Lys—Cys—Tyr—Lys—Gly—Tyr—Cys—Tyr—Arg—Lys—Cys—Arg —NH₂ | 54 | 0.005 | 10800 |
| | (2) | Arg—Arg—Trp—Cys—Tyr—Arg—Lys—Cys—Tyr—Lys—Gly—Tyr—Cys—Tyr—Arg—Lys—Cys—Arg—Arg—NH₂ | 200 | 1.26 | 159 |
| | (3) | Arg—Trp—Cys—Tyr—Arg—Lys—Cys—Tyr—Lys—Gly—Phe—Cys—Tyr—Arg—Lys—Cys—Arg —NH₂ | 50 | 0.07 | 714 |
| | (4) | Arg—Trp—Cys—Tyr—Arg—Lys—Cys—Tyr—Lys—Gly—Tyr—Cys—Tyr—Arg—Lys—Cys—Arg—Arg—NH₂ | 338 | 2.75 | 123 |
| | (7) | Arg—Arg—Tyr—Cys—Tyr—Arg—Lys—Cys—Tyr—Lys—Gly—Tyr—Cys—Tyr—Arg—Lys—Cys—Arg —NH₂ | 100 | 0.36 | 278 |
| | (12) | Arg—Arg—Trp—Cys—Tyr—Lys—Arg—Cys—Tyr—Lys—Gly—Tyr—Cys—Tyr—Lys—Arg—Cys—Arg —NH₂ | 245 | 0.49 | 500 |
| | (13) | Arg—Arg—Trp—Cys—Tyr—Arg—Lys—Cys—Tyr—Arg—Gly—Phe—Cys—Tyr—Arg—Lys—Cys—Arg —NH₂ | 52 | 0.009 | 5778 |
| | (14) | Arg—Arg—Trp—Cys—Tyr—Arg—Lys—Cys—Phe—Lys—Gly—Tyr—Cys—Tyr—Arg—Lys—Cys—Arg —NH₂ | 52 | 0.018 | 2889 |
| | (20) | Arg—Arg—Trp—Cys—Tyr—Arg—Lys—Cys—Tyr—Lys—Gly—Phe—Cys—Tyr—Arg—Lys—Cys—Arg —NH₂ | 54 | 0.01 | 5400 |
| | (21) | Arg—Trp—Cys—Tyr—Arg—Lys—Cys—Phe—Lys—Gly—Phe—Cys—Tyr—Arg—Lys—Cys—Arg —NH₂ | 53 | 0.08 | 663 |
| | (26) | Lys—Trp—Cys—Phe—Arg—Val—Cys—Tyr—Arg—Gly—Ile—Cys—Tyr—Arg—Arg—Cys—Arg —NH₂ | 165 | 0.18 | 917 |
| Prior Art High Endotoxin Affinity Polypeptides | Tachyplesin I | Lys—Trp—Cys—Phe—Arg—Val—Cys—Tyr—Arg—Gly—Ile—Cys—Tyr—Arg—Arg—Cys—Arg —NH₂ | 49 | 18.1 | 3 |
| | Tachyplesin II | Arg—Trp—Cys—Phe—Arg—Val—Cys—Tyr—Arg—Gly—Ile—Cys—Tyr—Arg—Lys—Cys—Arg —NH₂ | 36 | 6.6 | 6 |
| | Polyphemusin I | Arg—Arg—Trp—Cys—Phe—Arg—Val—Cys—Tyr—Arg—Gly—Phe—Cys—Tyr—Arg—Lys—Cys—Arg —NH₂ | 34 | 5.9 | 6 |
| | Polyphemusin II | Arg—Arg—Trp—Cys—Phe—Arg—Val—Cys—Tyr—Arg—Gly—Tyr—Cys—Tyr—Arg—Lys—Cys—Arg —NH₂ | 33 | 1.9 | 17 |
| Anti-HIV agent | AZT | | 6.8 | $4.8 \times 10^{-4}$ | 142 |

*1: (μg/ml)
*2: (μg/ml)
*3: (CC₅₀/EC₅₀)

TABLE IV

| Compd. Name | Compounds | | | | | | | | | | | | | | | | | |
|---|---|---|---|---|---|---|---|---|---|---|---|---|---|---|---|---|---|---|
| | 1' | 1 | 2 | 3 | 4 | 5 | 6 | 7 | 8 | 9 | 10 | 11 | 12 | 13 | 14 | 15 | 16 | 17 |
| (1) | Arg | Arg | Trp | Cys | Tyr | Arg | Lys | Cys | Tyr | Lys | Gly | Tyr | Cys | Tyr | Arg | Lys | Cys | Arg—NH2 |
| (3) | | Arg | Trp | Cys | Tyr | Arg | Lys | Cys | Tyr | Lys | Gly | Phe | Cys | Tyr | Arg | Lys | Cys | Arg—NH2 |
| (13) | Arg | Arg | Trp | Cys | Tyr | Arg | Lys | Cys | Tyr | Lys | Gly | Phe | Cys | Tyr | Arg | Lys | Cys | Arg—NH2 |
| (20) | Arg | Arg | Trp | Cys | Tyr | Arg | Lys | Cys | Cys | Phe | Gly | Phe | Cys | Tyr | Arg | Lys | Cys | Arg—NH2 |
| (21) | | Arg | Trp | Cys | Tyr | Arg | Lys | Cys | Phe | Lys | Gly | Phe | Cys | Tyr | Arg | Lys | Cys | Arg—NH2 |

| Compd. Name | Physical property $[\alpha]_D^{20\sim22}$ (Conc., Solvent) |
|---|---|
| (1) | +8.4° (C = 0.1, IN AcOH) |
| (3) | +20.0° (C = 0.1, IN AcOH) |
| (13) | +7.4° (C = 0.4, IN AcOH) |
| (20) | +8.2° (C = 0.6, IN AcOH) |
| (21) | +34.9° (C = 0.2, IN AcOH) |

The results shown in Table III indicate that the polypeptides synthesized in Example 1 have significantly higher anti-HIV activity as determined by effective concentration. Compounds (1), (3), (12), (13), (14), and (26), in particular were particularly selective in killing HIV infected cells. The selectivity index of compounds (1), (3), (12), (13), (14), and (26) were at least 7 fold higher than for any of the known high endotoxin affinity compounds.

The invention described and claimed herein is not to be limited in scope by the specific embodiments herein disclosed, since these embodiments are intended as illustrations of several aspects of the invention. Any equivalent embodiments are intended to be within the scope of this invention. Indeed various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. A polypeptide represented by the following formula (SEQ ID NO:6)

```
1    2    3    4   5   6    7    8   9   10  11
A₁ — A₂ — Cys — A₂ — A₃ — A₃ — Cys — A₂ — A₃ — Gly — A₂ —

12   13   14   15   16   17   18
                   — Cys — A₂ — A₃ — A₃ — Cys — A₄ — A₅
``` or salt thereof in which $A_1$ is a hydrogen or at least one and no more than two amino acids selected from the group consisting of lysine and arginine, $A_2$ is a tyrosine, phenylalanine or tryptophan residue, $A_3$ is an arginine or lysine residue, $A_4$ is at least one and no more than two amino acids selected from the group consisting of lysine and arginine, $A_5$ is an —OH or an $NH_2$, Cys is a cysteine residue, and Gly is a glycine residue.

2. The polypeptide or salt thereof of claim 1 in which $A_1$ is a hydrogen.

3. The polypeptide or salt thereof of claim 1 in which $A_1$ is at least one amino acid selected from the group consisting of lysine and arginine.

4. The polypeptide or salt thereof of claim 1 in which $A_1$ is two amino acids, in which said amino acids are selected from the group consisting of lysine and arginine.

5. The polypeptide or salt thereof of claim 1 in which $A_4$ is at least one amino acid selected from the group consisting of lysine and arginine.

6. The polypeptide or salt thereof of claim 1 in which $A_4$ is two amino acids, in which said amino acids are selected from the group consisting of lysine and arginine.

7. The polypeptide or salt thereof of claim 1 in which the cysteine residues at the 3- and 16-positions are linked through a disulfide linkage.

8. The polypeptide or salt thereof of claim 1 in which the cysteine residues at the 7- and 12-positions are linked through a disulfide linkage.

9. A polypeptide represented by the following formula (SEQ. ID NO:6)

$$\overset{1}{A_1}-\overset{2}{A_2}-\overset{3}{Cys}-\overset{4}{A_2}-\overset{5}{A_3}-\overset{6}{A_3}-\overset{7}{Cys}-\overset{8}{A_2}-\overset{9}{A_3}-\overset{10}{Gly}-\overset{11}{A_2}-$$

$$-\overset{12}{Cys}-\overset{13}{A_2}-\overset{14}{A_3}-\overset{15}{A_3}-\overset{16}{Cys}-\overset{17}{A_4}-\overset{18}{A_5}$$

or salt thereof in which $A_1$ is a hydrogen or at least one and no more than two amino acids selected from the group consisting of lysine and arginine, $A_2$ is a tyrosine, phenylalanine or tryptophan residue, $A_3$ is an arginine or lysine residue, $A_4$ is at least one and no more than two amino acids selected from the group consisting of lysine and arginine, $A_5$ is an —OH or an $NH_2$, Cys is a cysteine residue, and Gly is a glycine residue; and the cysteine residues at the 3- and 16-positions are linked through a disulfide linkage, and the cysteine residues at the 7- and 12-positions are linked through a disulfide linkage.

* * * * *